US010342485B2

(12) United States Patent
Lin et al.

(10) Patent No.: US 10,342,485 B2
(45) Date of Patent: Jul. 9, 2019

(54) REMOVABLE BASE FOR WEARABLE MEDICAL MONITOR (71) Applicant: COVIDIEN LP, Mansfield, MA (US)

(72) Inventors: Andy S. Lin, Boulder, CO (US); Friso Schlottau, Lyons, CO (US); David B. Berlin, Niwot, CO (US); Paul Von Der Lippe, Loveland, CO (US); Kristine Michelle Cohrs, Westminster, CO (US); Mark Yu-Tsu Su, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 705 days.

(21) Appl. No.: 14/869,481

(22) Filed: Sep. 29, 2015

(65) Prior Publication Data

US 2016/0095550 A1    Apr. 7, 2016

Related U.S. Application Data (60) Provisional application No. 62/058,315, filed on Oct. 1, 2014.

(51) Int. Cl.
| *A61B 5/00* | (2006.01) |
| *A61B 19/00* | (2006.01) |
| *A61B 5/024* | (2006.01) |
| *A61B 5/1455* | (2006.01) |

(52) U.S. Cl.
CPC .......... *A61B 5/6831* (2013.01); *A61B 5/0022* (2013.01); *A61B 5/02438* (2013.01); *A61B 5/14551* (2013.01); *A61B 2019/442* (2013.01); *A61B 2019/448* (2013.01); *A61B 2560/0214* (2013.01); *A61B 2560/0443* (2013.01); *A61B 2560/0475* (2013.01); *A61B 2562/08* (2013.01)

(58) Field of Classification Search
CPC . A61B 5/02438; A61B 5/6831; A61B 5/0002; A61B 5/002; A61B 2560/0443
USPC ........................................................ 600/300
See application file for complete search history.

(56) References Cited

U.S. PATENT DOCUMENTS

| D341,659 S | 11/1993 | Homayoun |
| 5,810,736 A | 9/1998 | Pail |
| 5,891,021 A | 4/1999 | Dillon et al. |
| D439,981 S | 4/2001 | Kasabach |
| 6,466,809 B1 | 10/2002 | Riley |
| 6,979,812 B2 | 12/2005 | Al-Ali |
| 7,048,687 B1 | 5/2006 | Reuss et al. |
| 7,072,704 B2 | 7/2006 | Bucholz |
| 7,085,597 B2 | 8/2006 | Fein et al. |
| 7,181,264 B2 | 2/2007 | Wiesmann et al. |
| 7,197,357 B2 | 3/2007 | Istvan et al. |

(Continued)

FOREIGN PATENT DOCUMENTS

| EP | 1713385 | 10/2006 |
| JP | 26075354 A2 | 3/2006 |

(Continued)

*Primary Examiner* — Gary Jackson
*Assistant Examiner* — Zahed Kabir
(74) *Attorney, Agent, or Firm* — Fletcher Yoder PC (57) ABSTRACT

A removable base of a wearable medical monitor includes a mating surface configured to reversibly couple the removable base to a body of the wearable medical monitor. The removable base may also include certain functional features, such as a sensor configured to detect a physiological parameter of a patient and/or a memory configured to store data for identifying characteristics of the sensor or the patient.

26 Claims, 5 Drawing Sheets

(56) References Cited

U.S. PATENT DOCUMENTS

| | | | |
|---|---|---|---|
| 7,201,734 B2 | 4/2007 | Hickle | |
| 7,247,154 B2 | 7/2007 | Hickle | |
| 7,248,910 B2 | 7/2007 | Li et al. | |
| 7,252,636 B2 | 8/2007 | Brown | |
| 7,272,245 B1 | 9/2007 | Al-Ali | |
| 7,316,648 B2 | 1/2008 | Kelly et al. | |
| 7,320,030 B2 | 1/2008 | Brown | |
| 7,387,607 B2 | 6/2008 | Holt et al. | |
| 7,392,074 B2 | 6/2008 | Isaacson et al. | |
| 7,400,257 B2 | 7/2008 | Rivas | |
| 7,423,526 B2 | 9/2008 | Despotis | |
| 7,438,687 B2 | 10/2008 | Lewicke | |
| 7,448,996 B2 | 11/2008 | Khanuja et al. | |
| 7,457,652 B2 | 11/2008 | Porges et al. | |
| D639,955 S | 6/2011 | Riobo et al. | |
| 7,978,063 B2 | 7/2011 | Baldus et al. | |
| D674,488 S | 1/2013 | McKay | |
| D677,792 S | 3/2013 | Vandiver | |
| D726,567 S | 4/2015 | De Jong et al. | |
| 2002/0178343 A1* | 11/2002 | Tsai | G06F 1/1626 712/1 |
| 2005/0101848 A1 | 5/2005 | Al-Ali et al. | |
| 2005/0165323 A1* | 7/2005 | Montgomery | A61B 5/0006 600/544 |
| 2005/0201345 A1 | 9/2005 | Williamson | |
| 2005/0251056 A1 | 11/2005 | Gribokov et al. | |
| 2006/0025660 A1 | 2/2006 | Swedlow et al. | |
| 2006/0030762 A1 | 2/2006 | David et al. | |
| 2006/0030763 A1 | 2/2006 | Mannheimer et al. | |
| 2006/0030764 A1 | 2/2006 | Porges et al. | |
| 2006/0030765 A1 | 2/2006 | Swedlow et al. | |
| 2006/0094936 A1 | 5/2006 | Russ | |
| 2006/0142808 A1 | 6/2006 | Pearce et al. | |
| 2006/0155589 A1 | 7/2006 | Lane et al. | |
| 2006/0161054 A1 | 7/2006 | Reuss et al. | |
| 2006/0167351 A1 | 7/2006 | Isaacson et al. | |
| 2006/0217604 A1 | 9/2006 | Fein et al. | |
| 2006/0217605 A1 | 9/2006 | Fein et al. | |
| 2006/0217606 A1 | 9/2006 | Fein et al. | |
| 2006/0217607 A1 | 9/2006 | Fein et al. | |
| 2006/0217608 A1 | 9/2006 | Fein et al. | |
| 2006/0224059 A1 | 10/2006 | Swedlow et al. | |
| 2006/0226974 A1 | 10/2006 | Fluegel | |
| 2006/0229503 A1 | 10/2006 | Fluegel | |
| 2006/0229510 A1 | 10/2006 | Fein et al. | |
| 2006/0229511 A1 | 10/2006 | Fein et al. | |
| 2006/0241975 A1 | 10/2006 | Brown | |
| 2006/0258295 A1 | 11/2006 | Wong et al. | |
| 2006/0258952 A1 | 11/2006 | Stahmann et al. | |
| 2006/0276714 A1 | 12/2006 | Holt et al. | |
| 2006/0285736 A1 | 12/2006 | Brown | |
| 2006/0288464 A1 | 12/2006 | Warden | |
| 2007/0004514 A1 | 1/2007 | Walker et al. | |
| 2007/0043269 A1 | 2/2007 | Mannheimer et al. | |
| 2007/0043270 A1 | 2/2007 | Mannheimer et al. | |
| 2007/0043271 A1 | 2/2007 | Mannheimer et al. | |
| 2007/0043272 A1 | 2/2007 | Mannheimer et al. | |
| 2007/0043273 A1 | 2/2007 | Mannheimer et al. | |
| 2007/0043274 A1 | 2/2007 | Mannheimer et al. | |
| 2007/0043275 A1 | 2/2007 | Mannheimer et al. | |
| 2007/0043276 A1 | 2/2007 | Mannheimer et al. | |
| 2007/0043277 A1 | 2/2007 | Mannheimer et al. | |
| 2007/0043278 A1 | 2/2007 | Mannheimer et al. | |
| 2007/0043279 A1 | 2/2007 | Mannheimer et al. | |
| 2007/0043280 A1 | 2/2007 | Mannheimer et al. | |
| 2007/0043282 A1 | 2/2007 | Mannheimer et al. | |
| 2007/0049810 A1 | 3/2007 | Mannheimer et al. | |
| 2007/0073116 A1 | 3/2007 | Kiani et al. | |
| 2007/0088207 A1 | 4/2007 | Mannheimer et al. | |
| 2007/0123756 A1 | 5/2007 | Kitajima et al. | |
| 2007/0129622 A1 | 6/2007 | Bourget et al. | |
| 2007/0149883 A1 | 6/2007 | Yesha | |
| 2007/0167850 A1* | 7/2007 | Russell | A61B 5/0205 600/513 |
| 2007/0185390 A1 | 8/2007 | Perkins | |
| 2008/0021379 A1 | 1/2008 | Hickle | |
| 2008/0030346 A1* | 2/2008 | Despotis | G08B 13/2434 340/572.9 |
| 2008/0060138 A1 | 3/2008 | Price et al. | |
| 2008/0088467 A1 | 4/2008 | Al-Ali | |
| 2008/0091089 A1 | 4/2008 | Guillory et al. | |
| 2008/0091090 A1 | 4/2008 | Guillory et al. | |
| 2008/0096495 A1 | 4/2008 | Shen | |
| 2008/0132798 A1 | 6/2008 | Hong et al. | |
| 2008/0142004 A1* | 6/2008 | Wasnick | A63B 23/18 128/200.24 |
| 2008/0177162 A1 | 7/2008 | Bae et al. | |
| 2008/0214903 A1 | 9/2008 | Orbach | |
| 2008/0221427 A1 | 9/2008 | Petersen | |
| 2008/0281168 A1 | 11/2008 | Gibson et al. | |
| 2008/0287757 A1 | 11/2008 | Berson et al. | |
| 2008/0319290 A1 | 12/2008 | Mao et al. | |
| 2009/0281394 A1 | 11/2009 | Russell et al. | |
| 2010/0160834 A1 | 6/2010 | Fong | |
| 2011/0003665 A1* | 1/2011 | Burton | G04F 10/00 482/9 |
| 2014/0162482 A1* | 6/2014 | Steuer | H01R 13/5202 439/271 |
| 2014/0221797 A1* | 8/2014 | Bailey | A61B 5/0002 600/324 |
| 2014/0286522 A1* | 9/2014 | Forbes | H04R 1/02 381/385 |
| 2014/0323818 A1* | 10/2014 | Axelgaard | A61B 5/0022 600/301 |
| 2015/0088007 A1* | 3/2015 | Bardy | A61B 5/0022 600/484 |
| 2015/0189134 A1* | 7/2015 | Joo | G06F 1/163 348/373 |
| 2015/0238094 A1* | 8/2015 | Lai | A61B 5/0002 600/301 |
| 2015/0305690 A1* | 10/2015 | Tan | G08B 21/0446 600/301 |
| 2015/0335284 A1* | 11/2015 | Nuovo | A61B 5/0022 600/301 |
| 2016/0051182 A1* | 2/2016 | Zabaleta Rekondo | A61B 5/6831 600/388 |
| 2016/0135431 A1* | 5/2016 | Sheldon | H02J 7/0047 119/859 |
| 2017/0020449 A1* | 1/2017 | Shim | A61B 5/7455 |

FOREIGN PATENT DOCUMENTS

| | | |
|---|---|---|
| JP | 26158555 A2 | 6/2006 |
| JP | 26158974 A2 | 6/2006 |
| JP | 26212161 A2 | 8/2006 |
| JP | 26271815 A2 | 10/2006 |
| JP | 26297125 A2 | 11/2006 |
| JP | 26320731 A2 | 11/2006 |
| JP | 26320732 A2 | 11/2006 |
| JP | 26325766 A2 | 12/2006 |
| JP | 27020836 A2 | 2/2007 |
| JP | 27117641 A2 | 5/2007 |
| JP | 3939782 B2 | 7/2007 |
| JP | 3944448 B2 | 7/2007 |
| JP | 27190122 A2 | 8/2007 |
| JP | 27252767 A2 | 10/2007 |
| JP | 27295973 A2 | 11/2007 |
| JP | 27319247 A2 | 12/2007 |
| JP | 27330708 A2 | 12/2007 |
| JP | 4038280 B2 | 1/2008 |
| JP | 28110108 A2 | 5/2008 |
| JP | 28161657 A2 | 7/2008 |
| WO | 05074379 | 8/2005 |
| WO | 05110215 | 11/2005 |
| WO | 06005169 A1 | 1/2006 |
| WO | 06109072 A2 | 10/2006 |
| WO | 07017777 A2 | 2/2007 |
| WO | 07086856 | 8/2007 |

\* cited by examiner

REMOVABLE BASE FOR WEARABLE MEDICAL MONITOR

CROSS-REFERENCE TO RELATED APPLICATION

This application claims priority to U.S. Provisional Application No. 62/058,315, filed Oct. 1, 2014, the disclosure of which is hereby incorporated by reference in its entirety for all purposes.

BACKGROUND

The present disclosure relates generally to wearable medical monitors and, more particularly, to wearable medical monitors that include removable bases.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A wearable medical monitor is a device worn on the body of a patient that is able to capture data about the patient's physiology to allow caregivers to monitor a patient's clinical condition. A wearable medical monitor may include or be coupled to one or more sensors attached to the body of the patient that detect and monitor the physiological parameters of the patient. A variety of types of wearable medical monitors may be used in conjunction with a variety of monitoring techniques, such as photoplethysmography, pulse oximetry, regional saturation oximetry, heart rate, electrocardiography (ECG), electroencephalography (EEG), electromyography (EMG), and glucose/insulin concentration monitoring.

However, to monitor a number of patients with different medical conditions, a medical facility (e.g., hospital, laboratory, or testing center) may employ a variety of types of wearable medical monitors. In addition, as the number of patients increases, a greater number of wearable medical monitors may be used. As such, the cost and complexity of using, cleaning, and identifying each wearable medical monitor may increase. For example, reusable wearable medical monitors may be cleaned and sterilized after being used for each patient. Moreover, every time a wearable medical monitor has been switched from one patient to another, an operator (e.g., doctor, nurse) may then program/reprogram the wearable medical monitor for the new patient and/or input/reinput the new patient's information (e.g., name, date of birth, type of measurement) to the wearable medical monitor or a downstream monitoring device. As such, the efficiency of operation may decrease.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Provided herein are wearable monitors that include portions that are separable from one another. In certain embodiments, the wearable medical monitors include a removable base, such as a patient-worn bracelet or strap, and a reusable body that may, in certain embodiments, include more expensive components and, for example, a robust housing that is capable of being sterilized for multiple uses. The body is capable of being reversibly coupled to the removable base by an operator. After use, a caregiver may dispose of the removable base while retaining and cleaning the reusable portion for use with the same patient or for different patients.

In certain embodiments, the removable base is "dumb," and contains little to no functionality other than coupling the body to the patient and limiting the direct contact of the reusable portion with the patient's skin. Such an embodiment may provide cost benefits, because the removable base may be formed from less expensive materials that are not graded for repeated sterilization and/or autoclaving. In other embodiments, certain functionality of the wearable medical monitor is contained in the removable base. For example, the removable base may include a memory or tag for storing identifying characteristics of the patient. Alternatively or additionally, the removable base may include one or more sensing components, a power source, a control switch, a communication device, etc. While such an embodiment may be relatively more expensive than a "dumb" removable base, the functionality housed within the removable base may allow caregivers to rapidly connect the appropriate body with the appropriate removable base without manually inputting calibration parameters or patient information. Further, certain electrical components that are relatively inexpensive but difficult to sterilize may also be included in the removable base. The removable base may be coupled to the patient for an extended period of time (e.g., during the entire stay of a hospital), and the body of the wearable medical monitor may be coupled to the removable base to obtain data related to one or more physiological parameters of the patient only during a monitoring period. Further, one body of the wearable medical monitor may be used (in series) with a number of removable bases that are each attached to different patients.

In particular embodiments, the removable base may include a sensor that may be attached to the patient. The removable base may also include a memory that stores data for identifying characteristics of the sensor (e.g., the type of the sensor, the operating parameters of the sensor). When the body of the wearable medical monitor is coupled to the removable base, a connection (e.g., wired or wireless) may be established for communicating data and other signals between the wearable portion, e.g., the removable base, and the body. For example, the memory may transfer the data for identifying characteristics of the sensor to a processor of the body, and the processor may execute routines and/or instructions stored in the body to direct the sensor on the removable base to obtain physiological parameters of the patient. Data related to the physiological parameters of the patient obtained from the sensor may be transferred via the connection to the body, which may further process the data and/or may transfer the data to a central control system (e.g., an electronic medical record). In particular embodiments, a single body may be configured to be used with a number of different types of sensors that may be attached to one or more patients, thereby increasing the flexibility of the monitoring system.

As noted, additional benefits of the present techniques may include automatic correlation of patient identification with an attached body via the removable base. For example, the identifier may be a barcode or an RFID chip coupled to or otherwise disposed on the removable base. The body may include a reader configured to read the data for identifying the patient from the removable base. Additionally or alternatively, the memory of the removable base may store the data for identifying the patient. The memory may transfer such data to the body, when the removable base is coupled to the body. The body may further transfer the data for identifying the patient to the central control system such that a patient's information and the obtained data related to the physiological parameter of the patient may be readily matched. This would reduce and/or eliminate the operator's input/reinput patient's information each time when the body is coupled to the removable for monitoring.

Moreover, in accordance with certain embodiments of the present disclosure, the removable base may also control activation of the body, e.g., via a switch configured to activate the body of the wearable medical monitor only when the body is coupled to the removable base and to turn off the body when the body is decoupled from the removable base. As such, the switch may save the operator a step of turning on the body of the wearable medical portion before monitoring of the patient. The switch may also save the operator a step of turning off the body after monitoring to save battery power of the body. Further, the switch may also be configured to only activate compatible bodies, thus preventing incompatible sensors from being used. In certain embodiments, the removable base may include a power source (e.g., a battery) configured to provide power to the body for operation only when the body is coupled to the removable operation, thereby providing an energy-saving functionality to the wearable medical monitor.

Figure 1:
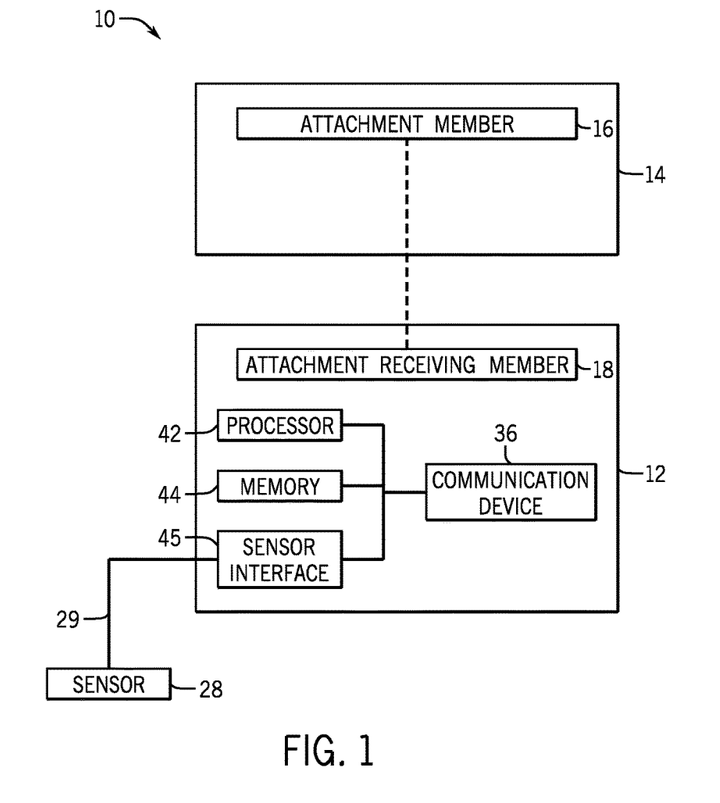
FIG. 1 is a block diagram of a wearable medical monitor including a removable base in accordance with the present disclosure.

With the foregoing in mind, FIG. 1 illustrates an embodiment of a wearable medical monitor 10 in accordance with the present disclosure. The wearable medical monitor 10 includes a body 12 and a removable base 14. As discussed in detail below, the removable base 14 may be reversibly coupled to the body 12. When the body 12 is coupled to the removable base 14, a measurement may take place to obtain data related to a physiological parameter of the patient. The coupling may be facilitated via an attachment member 16 on the removable base 14 that couples to an attachment receiving member 18 on the body 12. That is, the body 12 is coupled to the removable base 14 via respective mating surfaces, e.g., an attachment member 16 and an attachment receiving member 18. The wearable medical monitor 10 may be used in conjunction with a variety of suitable medical sensors 28 (e.g., coupled to the body 12 via a cable 29) to conduct a variety of medical measurements of a patient, including, but not limited to, photoplethysmography, pulse oximetry, regional saturation oximetry, heart rate, ECG, EEG, EMG, glucose/insulin concentration, respiratory therapy, etc. The body 12 may include certain hardware features such as a wireless communication device 36 for wireless communication, a processor 42, a memory 44, and a sensor interface 45 (e.g., an interface to receive a sensor connector) to facilitate coupling of the sensor 28 to the body 12 for medical monitoring. The depicted embodiment shows a "dumb" removable base 14 configured to be used in conjunction with a body 12. In certain embodiments, the body 12 is reusable.

In particular embodiments, the memory 44 may store instructions that may be accessed by the processor 42 to control the operations of the sensor or sensors 28. The processor 42 may execute the instructions to control the operations of the sensor 28 to obtain data related to one or more physiological parameters of the patient. For example, depending on the sensor type, the processor 42 may control the operations of one or more emitters and/or one or more detectors. During operation, the data related to the one or more physiological parameters of the patient obtained by the sensor 28 may then be transferred to the processor 42. The memory 44 may store the algorithms and/or functions for processing the sensor signal and/or calculating physiological parameters, which may be executed by the processor 42 The memory 44 may also store other data, for example, the data for identifying the patient (e.g., name, age, gender, date of birth, admission date).

Figure 2:
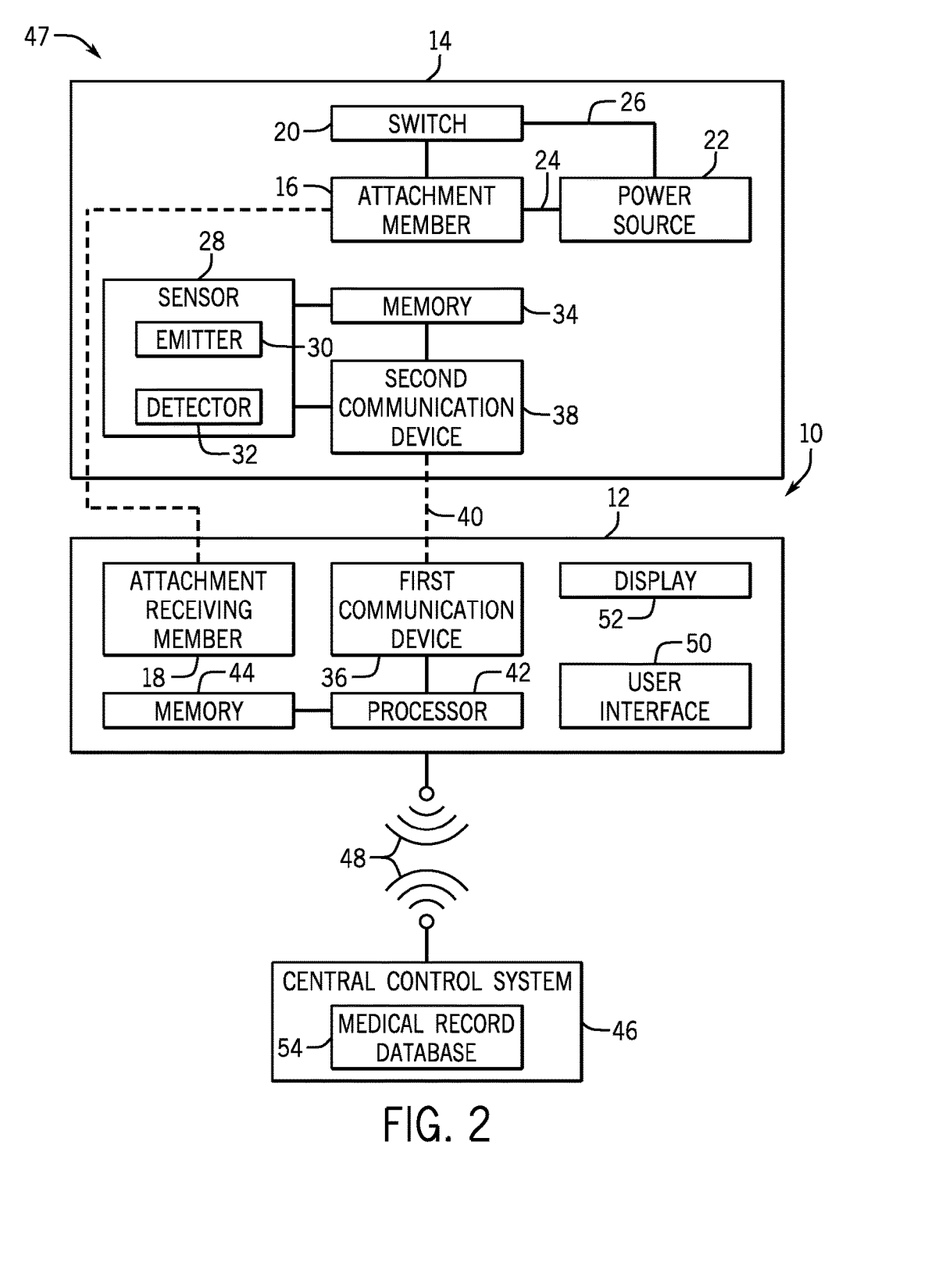
FIG. 2 is a block diagram of a wearable medical monitor including a removable base in accordance with the present disclosure.

FIG. 2 is a block diagram of a wearable medical monitor 10 in the context of a monitoring system 47. The system 47 may be used in conjunction with the wearable medical monitor 10 of FIG. 1. As noted with regard to FIG. 1, the removable base 14 may not include any processing or other hardware components, function to affix the functional components. Alternatively, as shown in FIG. 2, the wearable medical monitor 10 may be implemented with a removable base 14 that may include certain functional elements. However, it should be understood that the removable base 14 may include all or only one or more of such elements, and may include a switch 20, a power source 22, one or more conductors (24, 26), a sensor 28 such as an optical sensor including an emitter 30 and a detector 32, a memory 34, and a communication device 38.

For example, when present, the power source 22 (e.g., a non-rechargeable or rechargeable battery) is configured to provide power to the body 12 when the removable base 14 is coupled to the body 12. In one embodiment, the removable base 14 includes the conductor 24 coupling the power source 22 to the attachment member 16. When the attachment member 16 is coupled to the attachment receiving member 18 of the body 12, the power source 22 may provide power to the body 12 via the conductor 24. In another embodiment, the removable base 14 includes the conductor 26 coupling the power source 22 to the switch 20. When the removable base 14 is coupled to the body 12, the power source 22 may provide power to the body 12 via the switch 20. In another embodiment, the power source 22 includes one or more electrodes that may contact the body 12 (e.g., through certain one or more electrodes on the body 12), upon coupling the removable base 14 to the body 12, to provide power to the body 12.

The memory 44 may store instructions that may be accessed by the processor 42 to control the operations of the removable base 14. In some embodiments, the memory 34 of the removable base 14, in addition to the memory 44 of the body 12 or alternatively, may store the data for controlling the operation of the sensor or sensors 28. When a connection 40 (e.g., wired or wireless communication) between the removable base 14 and the body 12 is established, the processor 42 may access such data stored in the memory 34 to control the operations of the sensor 28 to obtain data related to one or more physiological parameters of the patient. In addition, the memory 34 may store identifier for identifying the removable base 14, such as a serial number, manufacturer, device code, or any combination thereof. Further, the memory 34 may store data (e.g., the detected signal) obtained by the sensor 28 related to the one or more physiological parameters of the patient.

The removable base 14 may be communicatively coupled to the body 12 via one or more communication devices. For example, the body 12 may include the first communication device 36 (e.g., a transceiver), and the removable base 14 may include the second communication device 38 (e.g., a transceiver). The first communication device 36 and the second communication device 38 are configured to communicate with each other via the connection 40 (e.g., wired, wireless, or a combination thereof). In one embodiment, the connection 40 is wired (e.g., via electrical conductors) and may be established when the removable base 14 is coupled to the body 12 and disconnected when the removable base 14 is decoupled from the body 12. In another embodiment, the connection 40 is wireless (e.g., via radio frequency, infrared, Bluetooth) and may be established when the removable base 14 is in proximity of the body 12. The second communication device 38 may be communicatively coupled to the memory 34. The data stored in the memory 34 may be transferred to the body 12 via the connection 40. In one embodiment, the second communication device 38 may be communicatively coupled to the sensor 28. The data obtained by the sensor 28 relating to the physiological parameter of the patient may be transferred to the body 12 via the connection 40 without being stored in the memory 34 first.

The body 12 may further transfer the data obtained from the removable base 14 to a downstream medical monitor (e.g., a pulse oximetry monitor) and/or central control system 46 via a connection 48. The connection 48 between the body 12 and the central control system 46 is a wireless connection as illustrated. However, any suitable connection 48, including a wired connection, may be used for communicatively coupling the body 12 to the central control system 46. The central control system 46 may include a medical record database 54. The medical record database 54 may include data for identifying the patient (e.g., name, age, gender, date of birth, admission date) and the medical record associated with the patient. When the removable base 14 is coupled to the body 12, the body 12 may direct the removable base 14 to obtain the data related to the physiological parameter of the patient based on the data for identifying the characteristics of the sensor 28 and/or the patient transferred from the removable base 14 to the body 12, as discussed above. The body 12 may then transfer the received data for identifying the characteristics of the sensor 28 and/or the patient and/or other data (e.g., unprocessed or processed data related to the physiological parameter of the patient) to the central control system 46. In some embodiments, the above described process (e.g., from attaching the body 12 to the removable base 14 to obtain the data related to the physiological parameter of the patient, to updating the medical record of the patient in the medical record database 54) may be automated (e.g., without intervention of an operator).

The body 12 may include a user interface 50 such that an operator (e.g., nurse, doctor, or clinician) may provide commands (e.g., control and/or operational commands) to the body 12. The user interface may include a mouse, keyboard, touch screen, writing pad, or any other suitable input and/or output devices. The commands may include directing the body 12 (e.g., the processor 42) to operate the removable base 14, directing the body 12 and the removable base 14 to communicate with each other including transferring data therebetween, directing the body 12 to communicate with other devices (e.g., another removable base, or a central control system, as discussed below), or any combination thereof. The body 12 may also include any suitable output devices, such as a display 52. The display 52 may be configured to display any suitable information processed by the processor 42, stored in the memory 44 of the body 12, provided by the removable base 14, or any combination thereof. In some embodiments, the user interface 50 and the display 52 may be combined together (e.g., using a touch screen).

Figure 3:
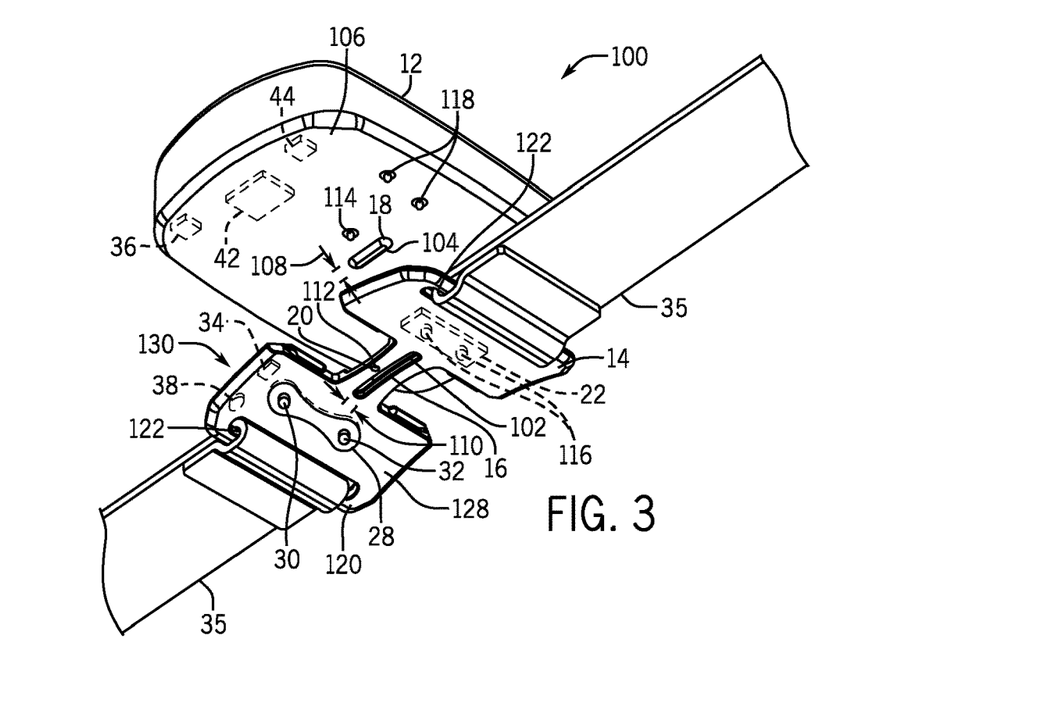
FIG. 3 is a perspective view of a wearable medical monitor including a removable base in accordance with an embodiment of the present disclosure.

FIG. 3 is a perspective view of an embodiment of a wearable medical monitor 100 (e.g., the wearable medical monitor 10 of FIG. 1 or FIG. 2) in accordance with the present disclosure that includes the removable base 14 and the body 12. The removable base 14 includes the attachment member 16, for example, an opening 102 in the removable base 14. The body 12 includes the attachment receiving member 18, for example, a protrusion 104 on a bottom surface 106 of the body 12. It should be understood that the positions of the protrusion 104 and the opening 102 may be exchanged. The protrusion 104 and the opening 102 may have any suitable size and are configured to be reversibly coupled to one another. For example, the protrusion 104 may have a width 108 that is slightly bigger than a width 110 of the opening 110, and the opening 102 may be elastically expandable. The protrusion 104 may be inserted into and held by the opening 102, and the protrusion 104 and the opening 102 may be separated from each other by pulling the protrusion 104 out of the opening 102. As such, the body 12 and the removable base 14 may be reversibly coupled to one another. The attachment member 16 may be coupled to the attachment receiving member 18 in any suitable manner, including, but not limited to, mechanically, electronically, and magnetically. For example, as discussed herein, the attachment receiving member 18 may include a mating feature, such as a raised (e.g., a hump, bulge, flange, or heave) or depressed part (e.g., a dent, hole, or concave) with respect to a back side of the body 12 that couples to a complementary feature on the attachment member 16 such that the attachment member 16 may be mechanically clipped onto and off from the attachment receiving member 18. In other embodiments, the attachment member 16 may be a clip and an engagement surface of the attachment receiving member 18. The mating surfaces of the attachment member 16 and the attachment receiving member 18 may include a mechanical lock, a junction, a fixture, a latch, a hook and loop engagement, a groove, a threaded surface, etc.

In embodiments in which the removable base 14 includes the switch 20 (e.g., a protrusion 112), the switch 20 may be configured to push an on/off button 114 disposed on the body 12 when the removable base 14 is coupled to the body 12, thereby turning on the body 12. When the removable base 14 is decoupled from the body 12, the protrusion 112 is configured to release the on/off button 114, thereby turning off the body 12. It should be noted that the switch 20 may operate in any suitable manner (e.g., mechanically, electrically, magnetically, or any combination thereof) to turn on the body 12 when the removable base 14 is coupled to the body12 and turn off the body 12 when the removable base 14 is decoupled from the body 12. For example, the switch 20 may include a conductive trace configured to complete a conductive circuit of the body 12 to turn on the body 12 when the removable base 14 is coupled to the body 12 and to return the conductive circuit to its incomplete state to turn off the body 12 when the removable base 14 is decoupled from the body 12. As another example, the switch 20 may include a wireless transmitter configured to send a wireless signal to turn on the body 12 (e.g., sensed by a sensor in the body 12) when the removable base 14 is coupled to or in a close proximity of the body 12 and to turn off the body 12 when the removable base 14 is decoupled from or beyond the close proximity of the body 12. Further, in embodiments in which the removable base 14 also includes the power source 22 (e.g., a non-rechargeable or rechargeable battery), the power source 22 may include a pair of electrodes 116. When the removable base 14 is coupled to the body 12, the pair of electrodes 116 of the power source 22 may contact a pair of electrodes 118 of the body 12 such that the power source 22 may provide power to the body 12 for operation via the two pairs of electrodes 116, 118. When the removable base 14 is decoupled from the body 12, the two pairs of electrodes 116, 118 are separated, thereby cutting off the power supply to the body 12.

The removable base 14 also includes a strap 35 coupled to a base section 120 of the removable base 14 via two openings 122 proximate to the two respective ends of base section 120. The strap 35 is configured to couple the removable base 14 to the patient, for example, wrapping around or otherwise attached to a body part (e.g., wrist, ankle, knee, chest, forehead, or the like) of the patient. In certain embodiments, the strap 35 may include an identifier (e.g., a barcode, an RFID chip, or a magnetic striped card) for identifying the patient. In one embodiment, the sensor 28 may be coupled to (e.g., attached to, disposed within) the strap 35. In another embodiment, a part of the sensor 28 (e.g., the emitter 30 or the detector 32) may be coupled to the strap 35. While the present techniques are disclosed in conjunction with a bracelet or strap 35, it should be understood that the removable base 14 may be affixed to the patient by any suitable structure, e.g., a hat, a headband, bandage, sock, adhesive, etc. The base section 120 includes a patient-facing surface 128 opposing a body contact surface 130. In the illustrated embodiment, the sensor 28 is disposed on or in the patient-facing surface 128. The body contact surface couples to the bottom surface 106 of the body 12.

Figure 4:
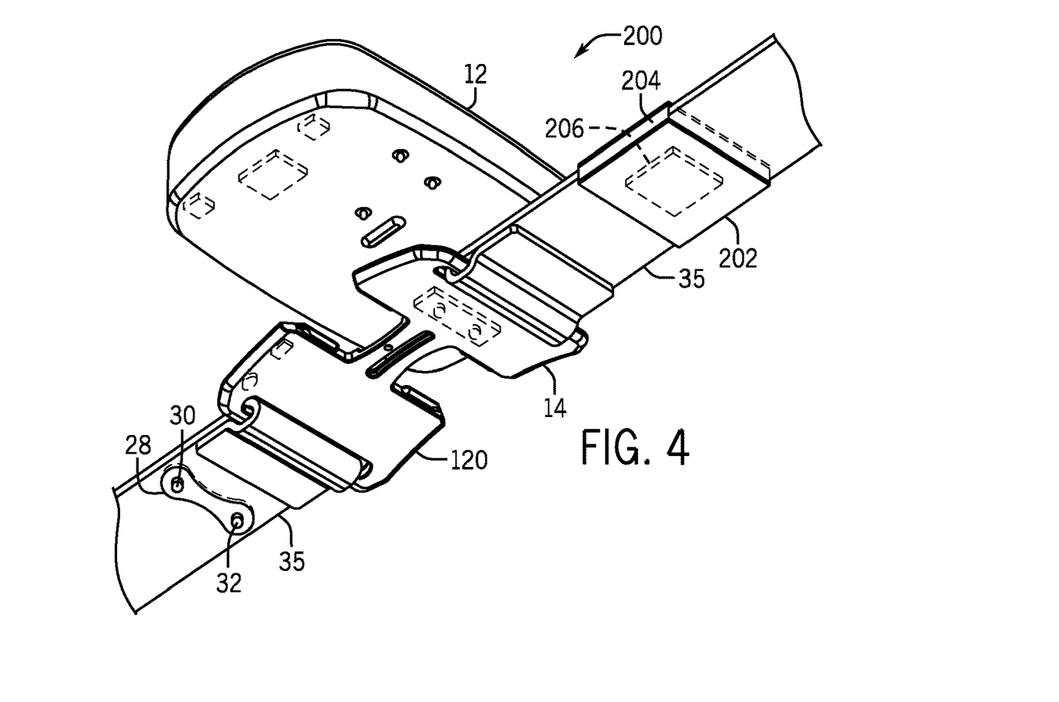
FIG. 4 is a perspective view of a wearable medical monitor including a removable base in accordance with another embodiment of the present disclosure.

In the depicted embodiment, the sensor 28 is disposed in, on, or otherwise attached to the base section 120 of the removable base 14. FIG. 4 is a perspective view of another embodiment of a wearable medical monitor 200 (e.g., the wearable medical monitor 10 of FIG. 1 or FIG. 2) in accordance with the present disclosure. The wearable medical monitor 200 illustrated in FIG. 4 is similar to the wearable medical monitor 100 illustrated in FIG. 3 except that the sensor 28 of the wearable medical monitor 200 is disposed on or integrated into the strap 35. Further, the strap 35 may be disposable, and the base section 120 of the removable base 14 may be reusable or disposable.

In addition, the removable base 14 of the wearable medical monitor 200 may include a sleeve 202. The sleeve 202 may be coupled to (e.g., slid onto, disposed on, attached to) the strap 35. The sleeve 202 may cover all or a portion of the strap 35. The sleeve may include a pocket 204, within which an identifier 206 may be disposed. The identifier 206 is configured for identifying the patient and may include a barcode, an RFID chip, a magnetic striped card, or the like. An identifier reader (e.g., a barcode reader, an RFID sensor, a card reader) included by, or separated from, the body 12 may read and/or transfer the data for identifying the patient to the central control system 46.

Figure 5:
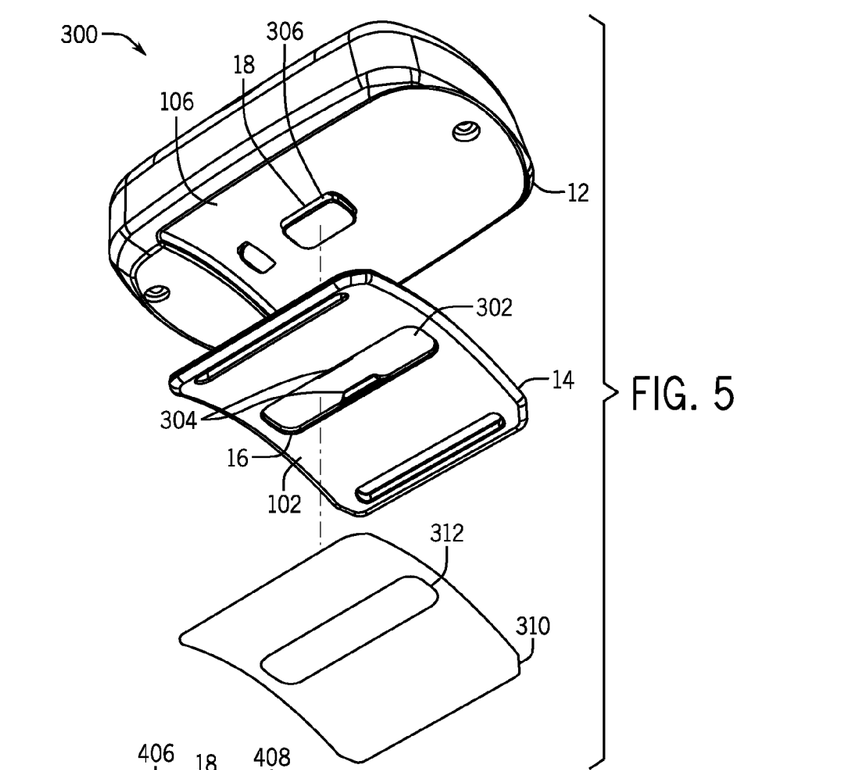
FIG. 5 is a perspective view of a removable base including an attachment member in accordance with an embodiment of the present disclosure.
Figure 6:
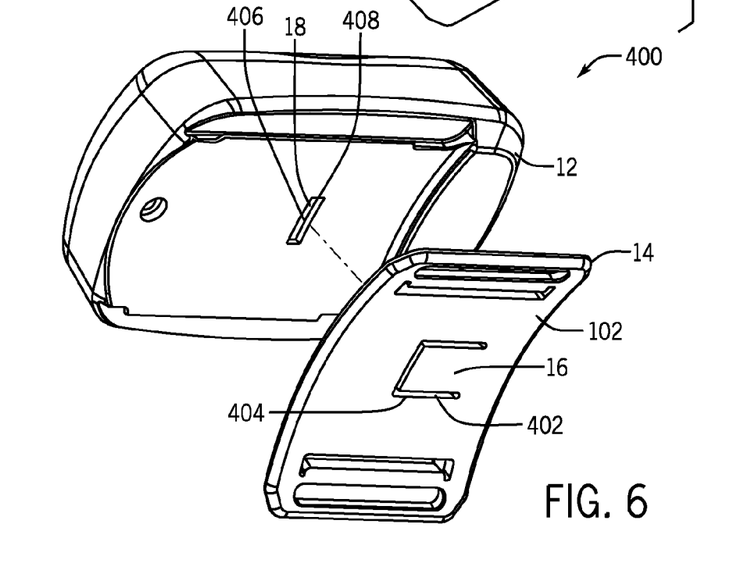
FIG. 6 is a perspective view of a removable base including an attachment member in accordance with another embodiment of the present disclosure.

FIGS. 5 and 6 illustrate embodiments of wearable medical monitors 300, 400 (e.g., the wearable medical monitor 10 of FIG. 1 or FIG. 2), respectively, in a perspective view. Each of the wearable medical monitors 300, 400 includes the body 12 and the removable base 14. For the purpose of simplification, various components of the wearable medical monitors 300, 400 are not explicitly illustrated or labeled.

The removable base 14 of the wearable medical monitor 300, as illustrated in FIG. 5, includes the attachment member 16, for example, an opening 302 in the base section 120. The attachment member 16 also includes a pair of tooth members 304 disposed generally on opposite sides of the opening 302. The body 12 includes the attachment receiving member 18, for example, a protrusion 306 on the bottom surface 106 of the body 12. The tooth members 304 are configured to hold onto the protrusion 306 when the opening 302 is coupled to the protrusion 306 such that the removable base 14 may be reversibly coupled to body 12. In addition, any of the disclosed removable bases 14 may be used in conjunction with a shield 310 (e.g., a pad) that is configured to directly contact the patient and further isolate the body 12 from direct contact with the patient for ease of cleaning. The shield 310 may also include one or more attachment members 312 (e.g., adhesive, bandage) that may be coupled to the existing attachment member 16 or may couple to other features on the removable base 14 or the body 12. The shield 310 may also be configured to carry the patient identification information, either via a memory, bar code, or tag, or written information.

The removable base 14 of the wearable medical monitor 400, as illustrated in FIG. 6, includes the attachment member 16, for example, a clipping piece 402 with generally rectangular shape positioned in the base section 120. Three sides of the clipping piece 402 have gaps 404 separating the clipping piece 402 from the rest of the base section 120 of the removable base 14. The other side of the clipping piece 402 is integrally attached to the base section 120. The body 12 includes the attachment receiving member 18, for example, a pocket 406 on the bottom surface 106 of the body 12. The pocket 406 includes an opening 408, via which the clipping piece 402 may be slid into the pocket 406, such that the removable base 14 may be reversibly coupled to body 12. It should be noted that the attachment member 16 and the attachment receiving member 18 of the wearable medical monitors 300, 400 illustrated in FIGS. 5 and 6 are examples for illustrative purposes and not meant to be limiting. Any suitable attachment member 16 and the attachment receiving member 18 configured to reversibly coupled the removable base 14 to the body 12 are contemplated herein.

Figure 7:
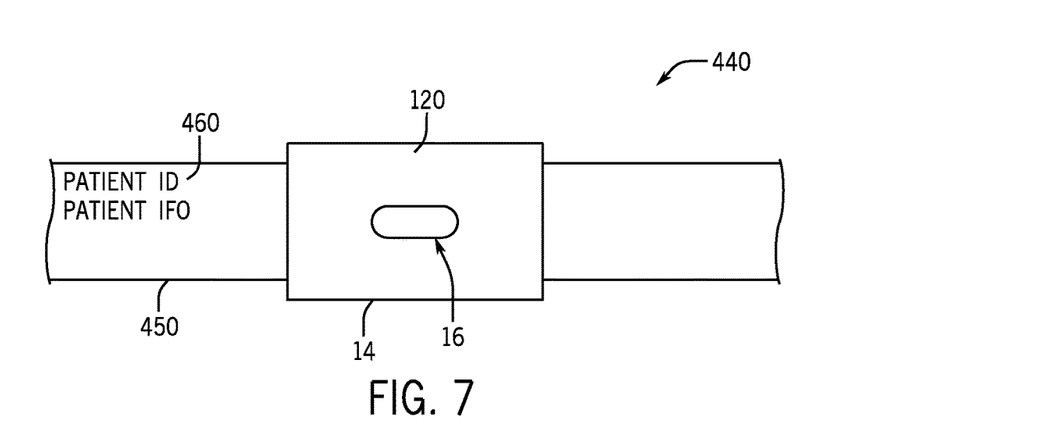
FIG. 7 is a perspective view of a removable base integrated into a hospital bracelet in accordance with another embodiment of the present disclosure.

FIG. 7 illustrates a hospital bracelet 440 including a removable base 14. In such an embodiment, the attachment member 16 and the base section 120 (and any present functional features of the removable base 14) may be part of a standard hospital bracelet 450 that includes printed information 460 such as patient ID and patient information including, for example, date of birth, admission date. Additionally or alternatively, the hospital bracelet 440 may include a scannable bar code for identifying the patient. In this manner, the body 12 may be coupled to the bracelet 450 that is already in place on each patient, which may simplify sensor application. Further, in hospitals that use a particular type of brand of sensor, the attachment member 16 may be dimensioned to only couple to bodies 12 of a particular type or from a particular manufacturer. The base section 120 may be formed from a material that is relatively more rigid than the hospital bracelet 450 to support the weight of the body 12 on the patient. Further, the base section 120 may be dimensioned to offset the body 12 away from the patient's skin to facilitate patient comfort.

Figure 8:
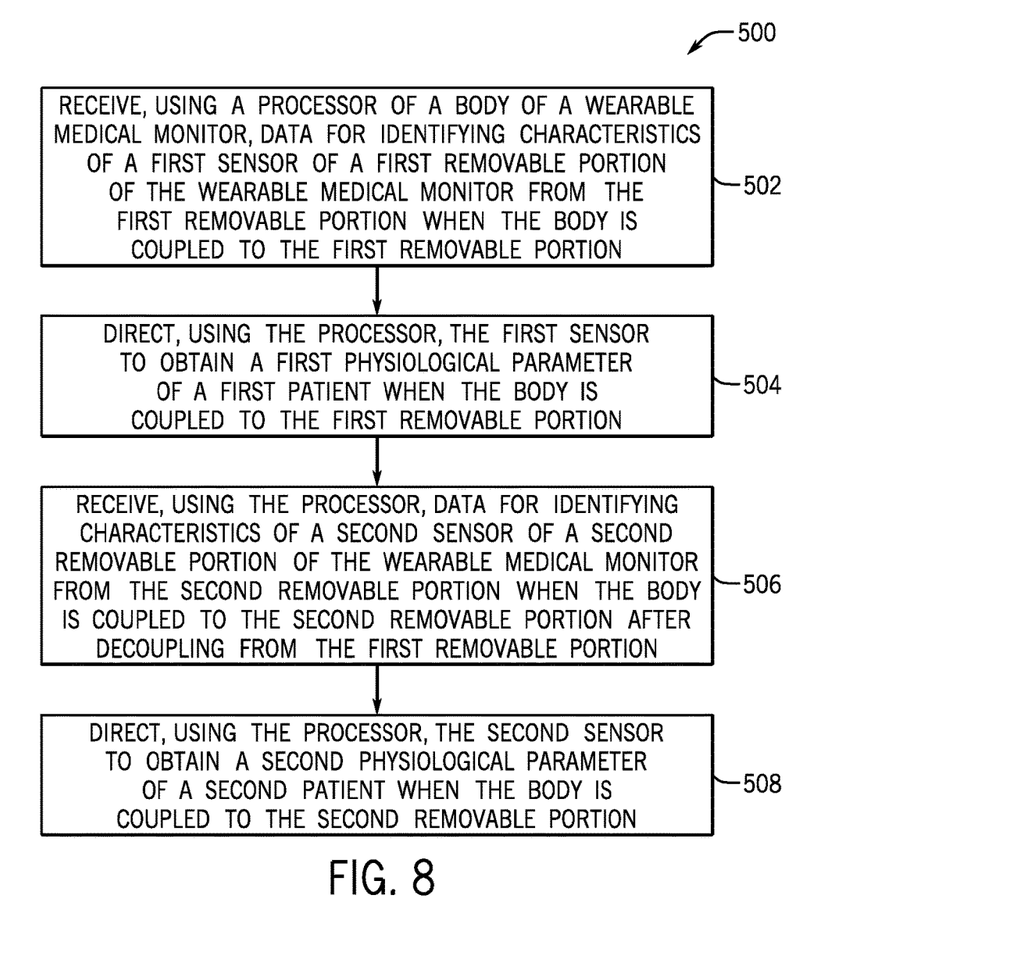
FIG. 8 is a flow diagram of a method for measuring physiological parameters with a wearable medical monitor in accordance with the present disclosure.

FIG. 8 is a flow diagram of a method 500 for measuring physiological parameters in accordance with the present disclosure with the wearable monitor 10. Because the removable base 14 may be reversibly coupled to the body 12, as described herein, one body 12 may be used with one or more removable bases 14, or one removable base 14 may be used with one or more bodies 12. For example, one body 12 may be used with multiple removable bases 14 that are attached to multiple patients to obtain the physiological parameters of the multiple patients.

The method 500 may start with receiving, using the processor 42 of the body 12 of the wearable medical monitor 10, the data for identifying characteristics of a first sensor 28 of a first removable base 14 of the wearable medical monitor 10 from the first removable base 14 when the body 12 is coupled to the first removable base 14 (block 502). The connection 40 is established when the body 12 is coupled to the first removable base 14, configured to provide communication between the first removable base 14 and the body 12. The data for identifying characteristics of a first sensor 28 may be stored in a first memory 34 disposed on the first removable base 14. The first removable base 14 may be attached to the first patient when the processor 42 receives the data for identifying characteristics of the first sensor 28. The first removable base 14 may include the strap 35 coupled to the two ends of the first removable base 14 and configured to couple the first removable base 14 with the first patient. In addition, the processor 42 may receive from the first removable base 14 other data including the data for identifying the first patient.

Based on the received data from the first removable base 14, the processor 42 may direct the first sensor 28 to obtain a first physiological parameter of the first patient (block 504). The processor 42 may also receive and/or the obtained first physiological parameter of the first patient from the sensor 28 (or via the first memory 34). The received and/or processed first physiological parameter of the first patient and/or other data including the data for identifying the first patient may be further communicated from the body 12 to the central control system 46.

The body 12 may then be decoupled from the first removable base 14 and coupled to a second removable base 14. The second removable base 14 may be attached a second patient (e.g., via the strap 35 coupled to the second removable base 14). Upon coupling the body 12 to the second removable base 14, the connection 40 may be established, configured to provide communication between the body 12 and the second removable base 14. The processor 42 may receive the data for identifying characteristics of a second sensor 28 of the second removable base 14 of the wearable medical monitor 10 from the second removable base 14 (block 506). Likewise, the processor 42 may receive from the second removable base 14 other data including the data for identifying the second patient.

Based on the received data from the second removable base 14, the processor 42 may direct the second sensor 28 to obtain a second physiological parameter of the second patient (block 508). The processor 42 may also receive and/or the obtained second physiological parameter of the second patient from the sensor 28 (or via the second memory 34). The received and/or processed second physiological parameter of the first patient and/or other data including the data for identifying the second patient may be further communicated from the body 12 to the central control system 46.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that elements of the disclosed embodiments may be combined or exchanged with one another.

What is claimed is:

1. A wearable medical monitor, comprising:
    a body comprising a first transceiver; and
    a removable base comprising a second transceiver, wherein the first transceiver and the second transceiver are configured for wireless communication with one another;
    mating surfaces on the body and the removable base positioned to reversibly couple the removable base to the body;
    a memory carried by the removable base, the memory configured to store data for identifying a patient; and
    a switch disposed on the removable base, the switch providing power to the body, wherein the switch comprises a protrusion configured to activate a button disposed on the body when the body is coupled to the removable base to provide the power.

2. The wearable medical monitor of claim 1, wherein the switch is deactivated when the removable base is decoupled from the body.

3. The wearable medical monitor of claim 1, comprising a power source carried by the removable base and configured to provide power to the body through the switch.

4. The wearable medical monitor of claim 1, comprising a sensor disposed on the removable base.

5. The wearable medical monitor of claim 4, wherein the sensor is configured to detect a physiological parameter of the patient and to communicate the physiological parameter of the patient to the body when the removable base is coupled to the body.

6. The wearable medical monitor of claim 5, wherein the body comprises a processor configured to access the memory to obtain data for identifying characteristics of the sensor and data for identifying characteristics of the patient.

7. The wearable medical monitor of claim 6, wherein the body comprises a transceiver configured to communicate the data for identifying characteristics of the sensor and the data for identifying characteristics of the patient to a central control system.

8. The wearable medical monitor of claim 6, wherein the processor is configured to communicate the data for identifying characteristics of the sensor to the body, and wherein the body is configured to control an operation of the sensor based on the data for identifying characteristics of the sensor when the removable base is coupled to the body.

9. The wearable medical monitor of claim 6, wherein the sensor comprises a plurality of sensors and wherein the processor is configured to access the memory to obtain identifying characteristics of each of the plurality of sensors, and wherein the body is configured to control an operation of each of the plurality of sensors based on the identifying characteristics of the respective sensor when the removable base is coupled to the body.

10. The wearable medical monitor of claim 1, wherein the removable base is disposable.

11. The wearable medical monitor of claim 1, wherein the removable base is coupled to a hospital identification bracelet.

12. The wearable medical monitor of claim 1, wherein the mating surfaces comprise a protrusion or a depression.

13. The wearable medical monitor of claim 1, wherein the mating surfaces comprise a clip and an engagement surface.

14. The wearable medical monitor of claim 1, comprising a shield coupled to a patient-facing surface of the removable base.

15. The wearable medical monitor of claim 14, wherein the shield is dimensioned to isolate the surface of the body from direct contact with the patient.

16. The wearable medical monitor of claim 1, comprising a display disposed on the body.

17. The wearable medical monitor of claim 16, wherein the display is a touch screen.

18. The wearable medical monitor of claim 1, comprising a user interface disposed on the body.

19. A wearable medical monitor, comprising:
a body comprising:
 a first transceiver;
 a processor configured to receive data from a physiological sensor;
 a memory configured to store the data; and
 a sensor port;
a conformable identification bracelet; and
a base carried by the conformable identification bracelet and relatively more rigid than the conformable identification bracelet, wherein the base is dimensioned to support the body, wherein the body is configured to detach from the base, and wherein the base comprises a second transceiver configured for wireless communication with the first transceiver, and a switch having a protrusion configured to activate a button on the body to turn on the body when the base is coupled to the body, and to release the button to turn off the body when the base is decoupled from the body, and
wherein the base comprises a mechanical lock engaging a complementary surface of the body to reversibly couple the base to the body.

20. The wearable medical monitor of claim 19, wherein the conformable identification bracelet comprises a hospital bracelet.

21. The wearable medical monitor of claim 19, wherein the base comprises a power source coupled to the switch and configured to provide power to the body.

22. The wearable medical monitor of claim 19, wherein the mechanical lock is dimensioned to couple to the complementary surface of the body but not to a second body of a different type.

23. The wearable medical monitor of claim 19, wherein the conformable identification bracelet comprises printed patient identification information.

24. The wearable medical monitor of claim 19, wherein the conformable identification bracelet comprises a bar code or RFID tag.

25. The wearable medical monitor of claim 19, comprising a display and a user interface disposed on the body.

26. The wearable medical monitor of claim 21, wherein the display and the user interface are part of a touch screen.

* * * * *